(12) United States Patent
White et al.

(10) Patent No.: US 6,635,136 B2
(45) Date of Patent: Oct. 21, 2003

(54) METHOD FOR PRODUCING MATERIALS HAVING Z-DIRECTION FIBERS AND FOLDS

(75) Inventors: Edward Jason White, Mauldin, SC (US); Kurtis Lee Brown, Alpharetta, GA (US); John Herbert Conrad, Alpharetta, GA (US); Robert James Gerndt, Roswell, GA (US); Jose Enrique Maldonado, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 214 days.

(21) Appl. No.: 09/841,477

(22) Filed: Apr. 24, 2001

(65) Prior Publication Data

US 2001/0054777 A1 Dec. 27, 2001

Related U.S. Application Data

(63) Continuation-in-part of application No. 09/538,744, filed on Mar. 30, 2000.
(60) Provisional application No. 60/199,922, filed on Apr. 26, 2000, and provisional application No. 60/199,925, filed on Apr. 26, 2000.

(51) Int. Cl.[7] .................................................. B31F 1/00
(52) U.S. Cl. ....................... 156/204; 156/227; 156/474; 156/181; 428/181; 428/182
(58) Field of Search ................................ 156/204, 205, 156/462, 474, 181, 227, 200–201, 459, 465; 428/181, 182, 105, 119, 176

(56) References Cited

U.S. PATENT DOCUMENTS

| 255,381 | A | | 3/1882 | Doubleday |
| 2,336,743 | A | | 12/1943 | Manning |
| 2,336,744 | A | | 12/1943 | Manning |
| 2,336,745 | A | | 12/1943 | Manning |
| 2,409,066 | A | * | 10/1946 | Powell et al. ............... 19/161.1 |
| 2,500,690 | A | * | 3/1950 | Lannan ........................ 156/474 |
| 2,510,229 | A | | 6/1950 | Joa |
| 2,886,877 | A | | 5/1959 | Frickert et al. |
| 2,931,091 | A | | 4/1960 | Breen |
| 2,975,470 | A | | 3/1961 | Snelson et al. |
| 3,012,923 | A | * | 12/1961 | Slayter ....................... 156/62.2 |
| 3,081,207 | A | | 3/1963 | Fox |

(List continued on next page.)

FOREIGN PATENT DOCUMENTS

| CS | 235 494 | 11/1986 |
| CS | 263 075 | 1/1990 |
| DE | 199 37 066 | 2/2000 |
| EP | 137 644 | 4/1985 |
| EP | 295 038 | 12/1988 |
| EP | 350 627 | 9/1994 |
| EP | 516 964 | 11/1996 |
| EP | 673 314 | 9/1998 |
| EP | 696 333 | 3/1999 |

OTHER PUBLICATIONS

Radko Krema et al.: *What's New In Highloft Production?*, Nonwovens Industry, 74–78, Oct. 1997.

Primary Examiner—Jeff H. Aftergut
Assistant Examiner—Jessica Rossi
(74) Attorney, Agent, or Firm—Pauley Petersen & Erickson

(57) ABSTRACT

A method for producing a material having z-direction ridges or folds in which a layer of continuous fibers is conveyed on a first moving surface into a nip formed by the first moving surface and a second moving surface which is traveling at a slower speed than the first moving surface, resulting in formation of a plurality of z-direction loops in the fibers giving loft to the material and a wave pattern producing ridges on both major surfaces of the resultant nonwoven web. The method permits easy real time adjustment of manufacturing parameters to produce a variety of materials. The method further produces lofty nonwovens at a commercially viable rate.

33 Claims, 6 Drawing Sheets

U.S. PATENT DOCUMENTS

| | | | |
|---|---|---|---|
| 3,086,253 | A | 4/1963 | Joa |
| 3,202,743 | A | 8/1965 | Elmendorf |
| 3,368,934 | A | 2/1968 | Vosburgh, Sr. |
| 3,481,005 | A | 12/1969 | Owens et al. |
| 3,589,956 | A | 6/1971 | Kranz et al. |
| 3,769,115 | A | 10/1973 | Rasmussen et al. |
| 3,802,817 | A | 4/1974 | Matsuki et al. |
| 3,849,241 | A | 11/1974 | Butin et al. |
| 3,972,092 | A | 8/1976 | Wood |
| 3,972,763 | A | 8/1976 | Wolvin et al. |
| 4,071,925 | A | 2/1978 | Folk |
| 4,089,720 | A | 5/1978 | Haley |
| 4,100,324 | A | 7/1978 | Anderson et al. |
| 4,102,963 | A | 7/1978 | Wood |
| 4,111,733 | A | 9/1978 | Periers |
| 4,340,563 | A | 7/1982 | Appel et al. |
| 4,357,379 | A | 11/1982 | Sloan et al. |
| 4,434,205 | A | 2/1984 | Fujii et al. |
| 4,440,597 | A | 4/1984 | Wells et al. |
| 4,488,928 | A | 12/1984 | Ali Khan et al. |
| 4,548,856 | A | 10/1985 | Ali Khan et al. |
| 4,582,666 | A | 4/1986 | Kenworthy et al. |
| 4,590,114 | A | 5/1986 | Holtman |
| 4,624,819 | A | 11/1986 | Hartog et al. |
| 4,741,941 | A | 5/1988 | Englebert et al. |
| 4,818,464 | A | 4/1989 | Lau |
| 4,837,067 | A | 6/1989 | Carey, Jr. et al. |
| 4,908,175 | A | 3/1990 | Angstadt |
| 4,955,999 | A | 9/1990 | Schaefer et al. |
| 5,021,050 | A | 6/1991 | Iskra |
| 5,071,615 | A | 12/1991 | Ranzen |
| 5,093,069 | A | 3/1992 | Mellem et al. |
| 5,093,963 | A * | 3/1992 | Farrington et al. ........... 19/296 |
| 5,108,827 | A | 4/1992 | Gessner |
| 5,167,740 | A | 12/1992 | Michaelis et al. |
| 5,198,057 | A | 3/1993 | Newkirk et al. |
| 5,227,107 | A | 7/1993 | Dickenson et al. |
| 5,366,793 | A | 11/1994 | Fitts, Jr. et al. |
| 5,382,400 | A | 1/1995 | Pike et al. |
| 5,558,924 | A | 9/1996 | Chien et al. |
| 5,620,545 | A | 4/1997 | Braun et al. |
| 5,658,640 | A | 8/1997 | Berrigan et al. |
| 5,702,801 | A * | 12/1997 | Chien .................. 428/181 |
| 5,707,468 | A | 1/1998 | Arnold et al. |
| 5,725,734 | A | 3/1998 | Herman et al. |
| 5,792,404 | A | 8/1998 | Cree et al. |
| 5,814,390 | A | 9/1998 | Stokes et al. |
| 5,930,871 | A * | 8/1999 | Raja ...................... 19/296 |
| 5,932,316 | A | 8/1999 | Cree et al. |
| 6,319,864 | B1 * | 11/2001 | Hannigan et al. ........... 442/281 |
| 6,331,268 | B1 * | 12/2001 | Kauschke et al. .......... 264/518 |

\* cited by examiner

METHOD FOR PRODUCING MATERIALS HAVING Z-DIRECTION FIBERS AND FOLDS

CROSS REFERENCE TO RELATED APPLICATIONS

This application is a continuation-in-part application of U.S. patent application Ser. No. 09/538,744, filed Mar. 30, 2000, and claims the benefit of U.S. Provisional Application Nos. 60/199,922, and 60/199,925, both filed Apr. 26, 2000 and also claims the benefit of U.S. Ser. No. 09/559,155, filed Apr. 26, 2000.

BACKGROUND OF THE INVENTION

1. Field of the Invention

This invention relates to a method for producing materials, including films and nonwovens, having z-direction folds or ridges on at least one surface of the material. This invention further relates to a lofty, nonwoven material produced from continuous fibers in which the lofty character of the nonwoven material is the result of the fibers comprising the web having a z-direction orientation, whereby a plurality of ridges or folds are formed on at least one surface of the nonwoven web. These materials may be particularly suitable for use in a broad range of applications including fluid management (surge), air and liquid filtration, acoustic and thermal insulation, packing material, absorbents, and cleaning materials. More particularly, these materials may be suitable for use as surge, spacer layers, filtration materials and absorbent layers in personal care absorbent products including disposable diapers, incontinence garments, and feminine care products such as sanitary pads and napkins, and in face masks, surgical gowns, sterile wraps and surgical drapes.

2. Discussion of the Related Art

Absorbent personal care articles such as sanitary pads and napkins, disposable diapers, incontinent-care pads and the like are widely used, and much effort has been made to improve their effectiveness and functionality. These articles generally include a liquid absorbent material backed by a liquid-impervious barrier sheet. To enhance the sense of comfort, the absorbent material has a facing of a material which masks at least the body-facing surface of the product. The purpose of this cover material is to help structurally contain the absorbent material and to protect the wearer from continuous direct contact with moisture from previously wetted absorbent material. The cover material is typically of relatively low basis weight nonwoven fabric. Improved product performance has been obtained in these products through the incorporation of a surge management material disposed between the cover material and the absorbent material. The surge management material is made from a relatively high basis weight, low density, that is, thick, nonwoven web material.

In nonwoven webs, the fibers comprising the web are generally oriented in the x-y plane of the web and the resulting nonwoven web material is relatively thin, that is lacking in loft or significant thickness. Loft or thickness in a nonwoven web suitable for use in personal care absorbent articles promotes comfort (softness) to the user, surge management and fluid distribution to adjacent layers.

In order to impart loft or thickness to a nonwoven web, it is generally desirable that at least a portion of the fibers comprising the web be oriented in the z-direction. Conventionally, such lofty nonwoven webs are produced using staple fibers. See, for example, U.S. Pat. No. 4,837,067 which teaches a nonwoven thermal insulating batt comprising structural staple fibers and bonding staple fibers which are entangled and substantially parallel to the faces of the batt at the face portions and substantially perpendicular to the faces of the batt, and U.S. Pat. No. 4,590,114 which teaches a batt including a major percent of thermomechanical wood pulp fibers stabilized by the inclusion of a minor percent of thermoplastic fibers including staple length thermoplastic fibers. Alternatively, conventional high loft forming processes rely on pre-forming processes such as fiber crimp formed on a flat wire or drum, and post-forming processes such as creping or pleating of the formed web.

SUMMARY OF THE INVENTION

In contradistinction to the known art, the present invention does not first form a web of material and pleat it. Rather, fibers are looped on themselves without first being formed into a material web. These fiber level loops, running from a first major surface of the web to a second major surface, are aggregated in the cross machine direction to form ridged structures herein sometimes called "waves" or "folds" to distinguish them from "pleats" which refer to structures in preformed web or mesh material that has been folded on itself. A "wavelength" may generally be considered the transit of a loop between its successive trough points on one major surface of the web.

Accordingly, it is one object of this invention to provide a lofty nonwoven web material comprising substantially continuous fibers as opposed to staple fibers traditionally used in the manufacture of such nonwoven materials.

It is yet another object of this invention to provide a method for producing nonwoven materials having z-direction orientation portions.

These and other objects of this invention are addressed by a method for producing a material having z-direction folds comprising conveying a substantially unformed and flat base material of substantially continuous fibers, and added materials if desired, on a first moving surface into a nip formed by the first moving surface and a second moving surface, the second moving surface traveling at a slower speed than the first moving surface, resulting in formation of a plurality of z-direction folds on at least one surface of the material. The method of this invention conveys a material by means of a moving surface into a confined space (the nip) and removes it from the confined space by means of a second moving surface, whereby the rate of removal of the material from the confined space is slower than the rate of material input to the confined surface, resulting in formation of a nonwoven material having z-direction components. The z-direction components produce ridges or ripples on both the major, or x-y surfaces of the material. According to this method the extent of the ridges, and thus the character of the resulting material formed, may be easily affected by a number of operating parameters including, but not limited to, the type of material being processed, geometry of the confined space, the means for transferring the material in the confined space from the first moving surface to the second moving surface, presence or lack of a binding agent such as an adhesive, and the relative speeds of the first and second moving surfaces.

Typically, the size of the confined space (nip) and the relative speeds of the moving surfaces are related with respect to the formation of a web having a desired density of folds. For example, for very low differential speeds between the two moving surfaces, the size of the nip will be very small. As the differential speeds increase, the size of the nip will also increase.

According to the embodiments herein, a material of this invention, as produced with the method of this invention, comprises a nonwoven web with a plurality of substantially continuous fibers having a z-direction orientation and forming a plurality of folds or ridges on the major surfaces of the nonwoven web.

In one embodiment according to the present invention a lofty nonwoven web, made with fibers looped on themselves, is made in a first configuration. This first configuration of the lofty web is made with regularly shaped ridges extending from the plane of the web in the z-direction, and occurring with regular pattern or periodicity in the machine (x-axis) or cross machine (y-axis) directions with the ridges lightly fixed in the first configuration. The first configuration of the ridges is broken and reset to a second predetermined configuration such as by controlled stretching. The ridges are then fixed in the second configuration, resulting in a new shape and periodicity of the ridges. The second configuration thus has no adhered leading or trailing edges of the ridge waveform. The second configuration is generally one which is unattainable through the process used to make the first configuration. The material is particularly useful for filtration media or other fabric structures where a known ridge shape and periodicity is desired. This embodiment may also be utilized for control of the periodicity and pleat shape of a previously pleated web.

In yet another embodiment, the present invention seeks to create, and utilize the advantages of, a lofty nonwoven web of continuous fibers having z-direction fibers but without discernable ridge structure which would lead to fluid channelization and other inherent characteristics of the ridge structure which may be undesirable for certain applications. Accordingly, among the objects of this embodiment is to provide a lofty nonwoven web material comprising substantially continuous fibers as opposed to staple fibers traditionally used in the manufacture of such nonwoven materials and to provide for producing nonwoven materials having z-direction portions with an undifferentiated mass of loops or pleats to create a web of material with no discernable ridge structure and no defined fluid channels.

In still another embodiment of the present invention, a precursor material having differential basis weight is formed using a three dimensional forming surface, which may be a wire or a formed membrane. Bands of higher and lower basis weight are thus formed, preferably running in the cross direction and alternating in the machine direction for the precursor web. The precursor material is then pleated, or folded, with the folds generally occurring along the borders between the higher and lower basis weight bands. The resultant lofty web material may then have major surfaces in x-y planes of a first basis weight material and interstitial material between the major surfaces in the z-direction composed of a second and different basis weight material. Alternatively, only one major surface may be higher basis weight material or, pleats of alternating high basis weight and low basis weight pleats may be produced in a single sheet. The material is particularly useful for fabric structures where a known ridge shape and periodicity is desired.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

As used herein, the term "nonwoven web" or "nonwoven material" means a web having a structure of individual fibers, filaments or threads which are interlaid, but not in a regular or identifiable manner such as those in a knitted fabric or films that have been fibrillated. Nonwoven webs or materials have been formed from many processes such as, for example, meltblowing processes, spunbonding processes, and bonded carded web processes. The basis weight of nonwoven webs or materials is usually expressed in ounces of material per square yard (osy) or grams per square meter (gsm), and the fiber diameters usable are usually expressed in microns. (Note that to convert from osy to gsm, multiply osy by 33.91.).

Figure 3A:
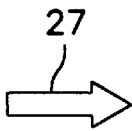
FIGS. 3A and 3B are diagrammatic representations of a conventional nonwoven web and a high loft nonwoven web in accordance with this invention, respectively.
Figure 3A:
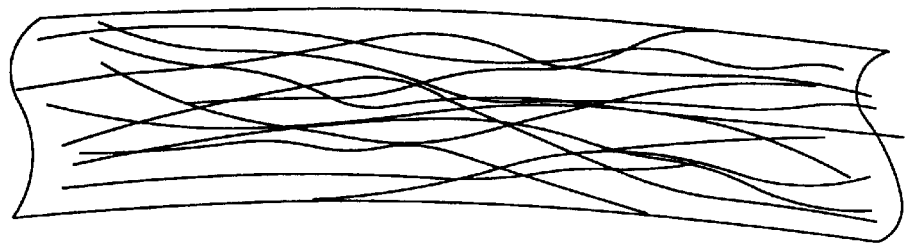
Figure 3B:
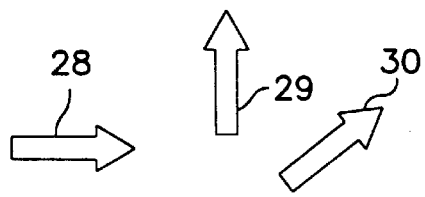
Figure 3B:
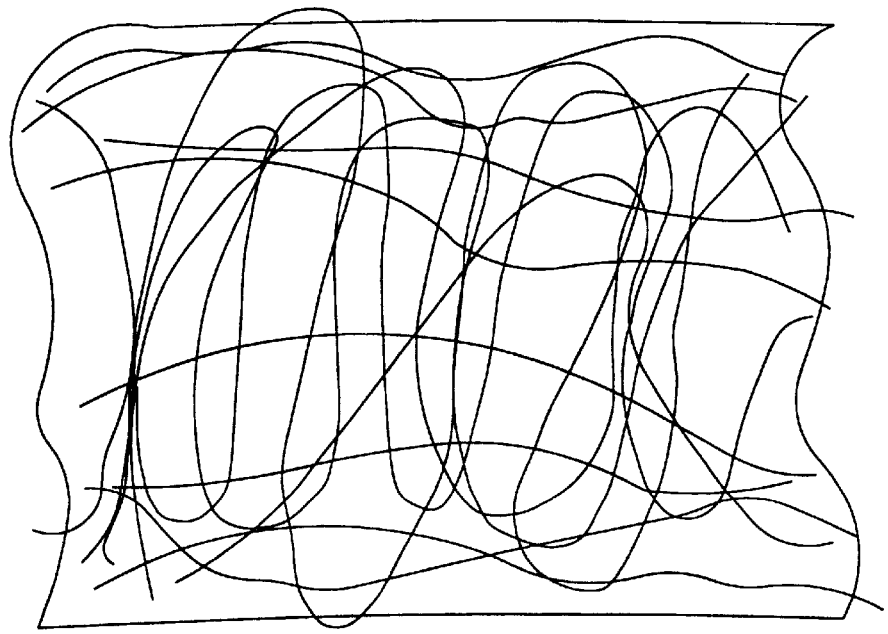

As used herein, the term "z-direction" refers to fibers disposed outside of the plane of orientation of a web. FIG. 3A is a diagram showing a nonwoven web without z-direction fibers. That is, all of the fibers are generally oriented in the direction indicated by arrow 27. By comparison, FIG. 3B is a diagram showing a nonwoven web having z-direction fibers in accordance with this invention. That is, in addition to fibers oriented in the direction of arrow 28, fibers are also oriented in the direction of arrows 29 and 30. The term "as formed z-direction fibers" as used herein refers to fibers that become oriented in the z-direction during forming of the nonwoven web as distinguished from fibers having a z-direction component resulting from post-forming processing of the nonwoven web, such as in the case of mechanically crimped or creped nonwoven webs.

As used herein, the term "spunbond fibers" refers to small diameter fibers which are formed by extruding molten thermoplastic material as filaments from a plurality of fine, usually circular capillaries of a spinneret as taught, for example, by U.S. Pat. No. 4,340,563 to Appel et al. and U.S. Pat. No. 3,802,817 to Matsuki et al.

As used herein, the term "meltblown fibers" refers to fibers formed by extruding a molten thermoplastic material through a plurality of fine, usually circular, die capillaries as molten threads or filaments into converging high velocity gas streams (for example, airstreams) which attenuate the filaments of molten thermoplastic material to reduce their diameter, which may be to microfiber diameter. Such a process is disclosed, for example, by U.S. Pat. No. 3,849,241 to Butin.

As used herein, the term "microfibers" refers to small diameter fibers having an average diameter not greater than about 75 microns, for example, having an average diameter of from about 0.5 microns to about 50 microns, or more particularly, having an average diameter of from about 2 microns to about 40 microns.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" also includes all possible geometric configurations of the material. These configurations include, but are not limited to, isotactic, syndiotactic, atactic and random symmetries.

As used herein, the term "personal care absorbent article" means disposable diapers, training pants, absorbent underpants, adult incontinence products, feminine hygiene products and the like.

As used herein, the term "homofilament" refers to a fiber formed from only one polymer. This is not meant to exclude fibers formed from one polymer to which small amounts of additives have been added for coloration, anti-static properties, lubrication, hydrophilicity, etc.

As used herein, the term "bicomponent fibers" refers to fibers which have been formed from at least two polymers extruded from separate extruders but spun together to form one fiber. Bicomponent fibers are also sometimes referred to as conjugate fibers or multicomponent fibers. Bicomponent fibers are taught by U.S. Pat. No. 5,382,400 to Pike et al.

As used herein, the term "biconstituent fibers" refers to fibers which have been formed from at least two polymers extruded from the same extruder as a blend. The term "blend" is defined below. Biconstituent fibers are sometimes also referred to as multiconstituent fibers. Fibers of this general type are discussed in, for example, U.S. Pat. No. 5,108,827 to Gessner. As used herein, the term "blend" means a mixture of two or more polymers.

As used herein, the term "substantially continuous fibers" refers to fibers, including without limitation, spunbond and meltblown fibers, which are not cut from their original length prior to being formed into a nonwoven web or fabric. Substantially continuous fibers may have average lengths ranging from greater than about 15 centimeters to more than one meter, and up to the length of the web or fabric being formed. The definition of "substantially continuous fibers" includes fibers which are not cut prior to being formed into a nonwoven web or fabric, but which are later cut when the nonwoven web or fabric is cut, and fibers which are substantially linear or crimped.

The term "staple fibers" means fibers which are natural or cut from a manufactured filament prior to forming into a web, and which have an average length ranging from about 0.1–15 centimeters, more commonly about 0.2–7 centimeters.

As used herein, the term "through-air bonding" or "TAB" means the process of bonding a nonwoven, for example, a bicomponent fiber web in which air which is sufficiently hot to melt one of the polymers of which the fibers of the web are made is forced through the web.

As used herein, the term "coform" means a process in which at least one meltblown diehead is arranged near a chute through which other materials are added to the base material or the web while it is forming. Such other materials may be pulp, superabsorbent particles, cellulose or staple fibers, for example. Coform processes are shown in commonly assigned U.S. Pat. No. 4,818,464 to Lau.

Figure 1:
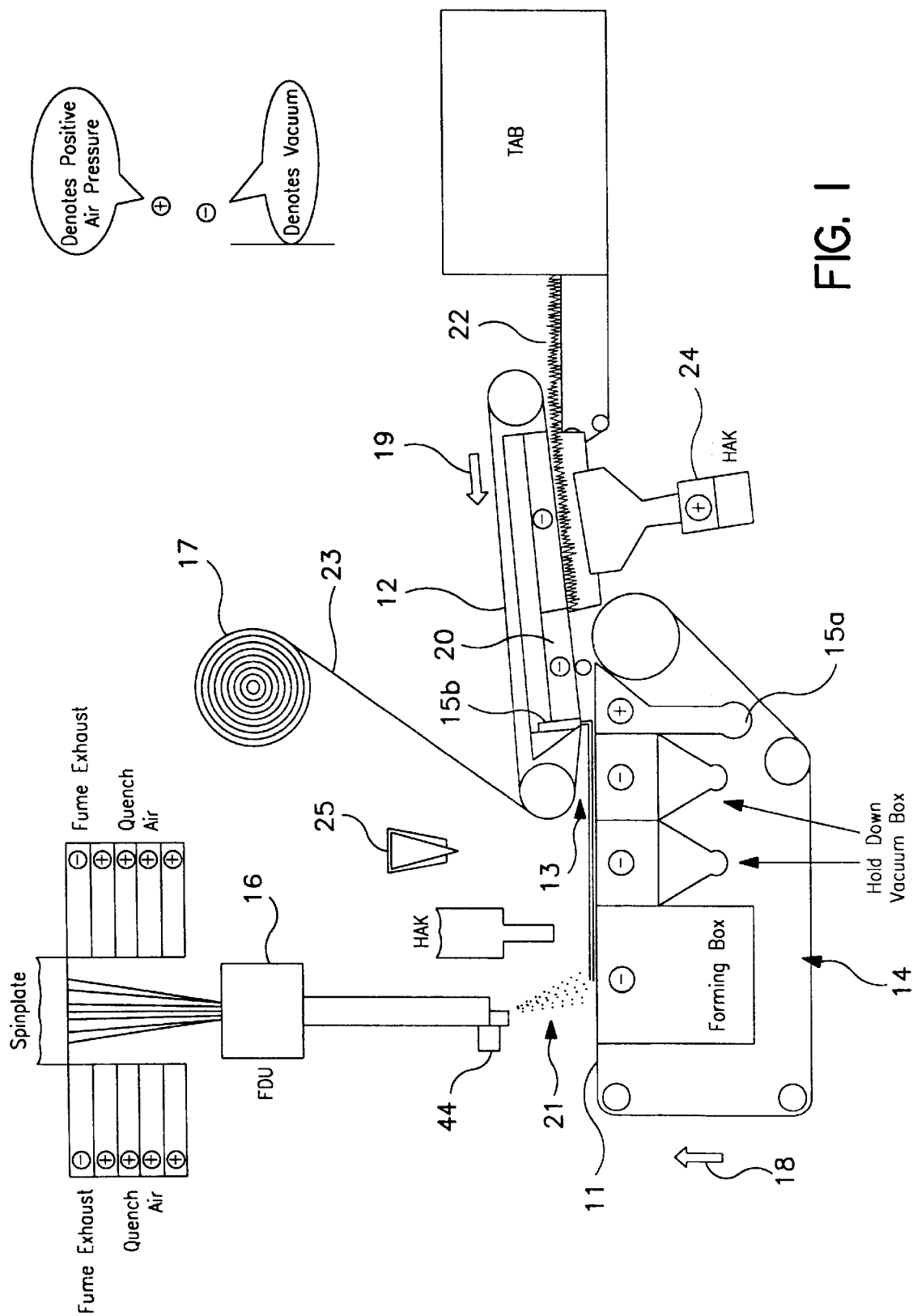
FIG. 1 is a schematic diagram of the method of this invention for producing materials having z-direction components.

FIG. 1 is a schematic diagram showing the method of this invention for producing materials including, but not limited to, films, nonwoven materials and woven materials having z-direction components in the form of ridges or peaks on at least one face. The ridges or peaks formed in accordance with the method of this invention may be regularly spaced or irregular in spacing and shape.

As shown in FIG. 1, a base material 21 of lightly, or nonfunctionally, bonded fibers is transported or conveyed on a first moving surface 11 into the confined space defined by nip 13 formed by first moving surface 11 and second moving surface 12. "Nonfunctionally bonded" is a bonding sufficient only to hold the fibers in place for processing according to the method herein but so light as to not hold the fibers together were there to be manipulated manually. Such bonding may be incidental or eliminated altogether if desirable. A coform unit 44 for adding additional materials to the y base material is attached near the outlet of the fiber distribution unit 16. First moving surface 11 is moving in the direction of arrow 18 at a given speed. Base material 21 is held down on first moving surface 11 by a hold down vacuum 14. In nip 13, base material is transferred to second moving surface 12 moving in the direction indicated by arrow 19 via positive air pressure from a blow up box 15a underneath first moving surface 11 and a transfer vacuum 20 beneath the second moving surface. The transfer of the material in nip 13 from first moving surface 11 to second moving surface 12 is accomplished by the application of a transfer vacuum beneath second moving surface 12 generated by high vacuum slot 15b and a transfer vacuum represented by reference numeral 20. It will be appreciated that the present invention may work without a true nip, that is, the first and second surfaces may be serially offset to such a degree that there is no true overlap in their opposite facing surfaces. Second moving surface is moving at a speed slower than the speed of first moving surface 11. First and second moving surfaces are normally foraminous or perforate, wire mesh belts, known in the art as "wires". In accordance with one preferred embodiment of this invention, the speed of first moving surface 11 is in the range of about 1.25 to about 7 times faster than the speed of second moving surface 12.

The confining nature of nip 13 is such that, as the base material 21 of fibers enters nip 13 and is taken away at a slower speed by second moving surface 12, base material 21 accumulates in nip 13 causing the fibers to bunch up and translate into a z-direction displacement until the volume of nip 13 is filled. More specifically, base material 21 moving in the direction indicated by arrow 18 encounters a slowdown in nip 13 as a result of which the base material 21 moves in the z-direction until it hits the surface of second moving surface 12 and is removed thereby. As a result, the material exiting from nip 13 comprises at least one surface, and normally both surfaces, having ridges or peaks as indicated by reference numeral 22.

Although suitable for producing ridged films and pleated wovens, the method of this invention is particularly suitable for producing preponderantly open, or low density, nonwoven webs of continuous fibers having z-direction components. Specifically, the material produced in accordance with a preferred embodiment of this invention is a nonwoven web comprising a plurality of substantially continuous fibers having a z-direction orientation and forming the ridges or peaks 22.

The substantially continuous fibers are preferably selected from the group consisting of homofilament fibers, bicomponent fibers, biconstituent fibers and combinations thereof. The substantially continuous fibers are preferably formed with polymers selected from the group consisting of polyolefins, polyamides, polyesters, polycarbonates, polystyrenes, thermoplastic elastomers, fluoropolymers, vinyl polymers, and blends and copolymers thereof.

Suitable polyolefins include, but are not limited to, polyethylene, polypropylene, polybutylene, and the like; suitable polyamides include, but are not limited to, nylon 6, nylon 6/6, nylon 10, nylon 12 and the like; and suitable polyesters include, but are not limited to, polyethylene terephthalate, polybutylene terephthalate and the like. Particularly suitable polymers for use in the present invention are polyolefins including polyethylene, for example, linear low density polyethylene, low density polyethylene, medium density polyethylene, high density polyethylene and blends thereof; polypropylene; polybutylene and copolymers as well as blends thereof. Additionally, the suitable fiber forming polymers may have thermoplastic elastomers blended therein. In addition, staple fibers may be employed in the nonwoven web as a binder.

In order to provide stability to the product material, the nonwoven web is bonded, either by application of an adhesive from adhesive system 25 or by thermal bonding such as by through-air bonding, a calender, or the like, or by means of a hot air knife (HAK) 24. A hot air knife is used to bond the individual polymer fibers together at various locations so that the web has increased strength and structural integrity for subsequent treatments such as passage through a through-air bonding (TAB) unit. A conventional hot air knife includes a mandrel with a slot that blows a jet of hot air onto the nonwoven web surface. Such hot air knives are taught, for example, by U.S. Pat. No. 5,707,468 to Arnold et al.

As shown in FIG. 1, a base material 21 of substantially continuous fibers is fed onto first moving surface 11 from a Fiber Distribution Unit 16 as at reference numeral 16. However, it will be apparent to those skilled in the art that certain base material 21 fibers may be formed directly on first moving surface 11 or unwound from prewound spools or the like.

Base materials suitable for use in the material and method of this invention are preferably selected from the group consisting of spunbond, meltblown, spunbond-meltblown-spunbond laminates, coform, spunbond-film-spunbond laminates, bicomponent spunbond, bicomponent meltblown, biconstituent spunbond, biconstituent meltblown, pulp, superabsorbent, and combinations thereof.

The characteristics of the material produced in accordance with the method of this invention may be varied by varying such method elements as nip geometry, including the vertical distance between first moving surface 11 and second moving surface 12 as well as the extent of overlap between first moving surface 11 and second moving surface 12, vacuum strength and location, bonding mechanism, and speeds of the material entering and leaving nip 13. The type of fiber will also have an affect on the morphology of the web made. In addition, although the present invention generally produces a self-supporting lofty web, the end product may include a support structure or a second material 23, as shown being introduced into nip 13 from the unwind designated by reference numeral 17.

Figure 2:
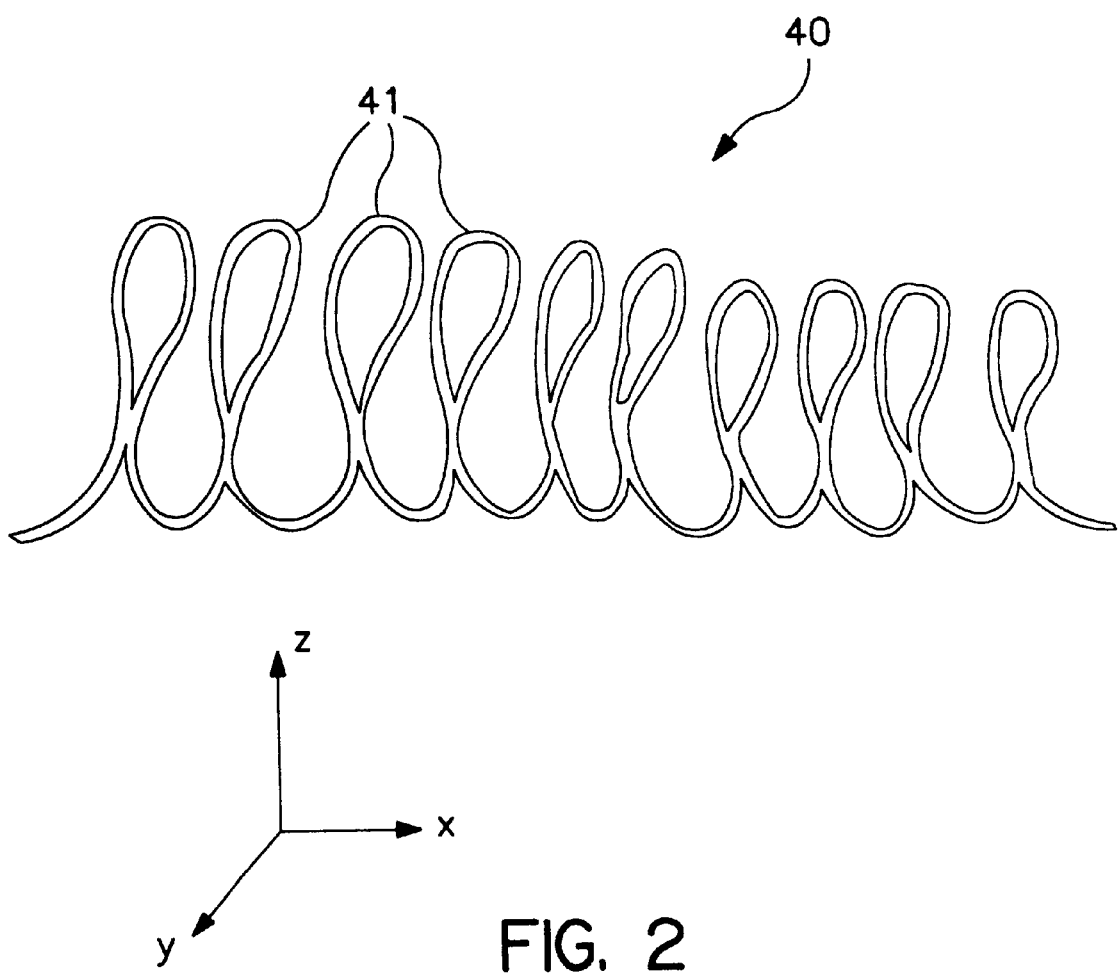
FIG. 2 is a diagram of a side view of a nonwoven web having z-direction components in the form of ridges or ripples formed in accordance with the method of this invention.

FIG. 2 is a diagram showing a side view of a z-direction component nonwoven web 40 produced in accordance with the method of this invention comprising folds 41 formed by substantially continuous fibers.

In accordance with one preferred embodiment of this invention, the substantially continuous fibers are bicomponent fibers. Particularly suitable polymers for forming the structural component of suitable bicomponent fibers include polypropylene and copolymers of polypropylene and ethylene, and particularly suitable polymers for the adhesive component of the bicomponent fibers includes polyethylene, more particularly linear low density polyethylene, and high density polyethylene. In addition, the adhesive component may contain additives for enhancing the crimpability and/or lowering the bonding temperature of the fibers, and enhancing the abrasion resistance, strength and softness of the resulting webs.

The nonwoven web of the material of this invention has a basis weight in the range of about 0.25 osy to about 50 osy. To enhance the absorption characteristics of the nonwoven material, in accordance with one embodiment of this invention, the nonwoven web comprises an absorbent, for example, superabsorbent particles. In accordance with one embodiment of this invention, a support structure is attached to at least one face of the nonwoven web so as to provide strength thereto. The resulting laminate structure provides support for the high loft structure, strength for winding, converting, etc., and a boundary layer to either enhance or retard fluid flow into the lofty absorbent structure. The support structure may include spunbond webs of various types including liners, perforated, micro-fiber, creped, etc., spunbond-meltblown-spunbond (SMS), meltblown, and/or films.

Potential applications for the nonwoven web of this invention include personal care absorbent articles such as diapers, training pants, incontinence garments, feminine care products including sanitary pads and napkins, all surge materials, loop for hook and loop, air filtration, liquid filtration, body scrub pads, oil sorb, industrial and baby wipes, insulation material, packaging material, and translucent or shading material for lamp shades or the like. In the case of filtration materials, the method of this invention greatly increases the surface area available for filtration. In addition, the method of this invention may be suitable for pleating fabrics. And, for rolls of diapers, a composite material could be produced by ridging or ruffling a high loft surge/pulp/superabsorbent material laminate and placing it in between an outer cover and a liner, which would produce a laminate with all of the components of a diaper in a single step, which could be wound up and cut and placed later on converting machines.

Figure 4:
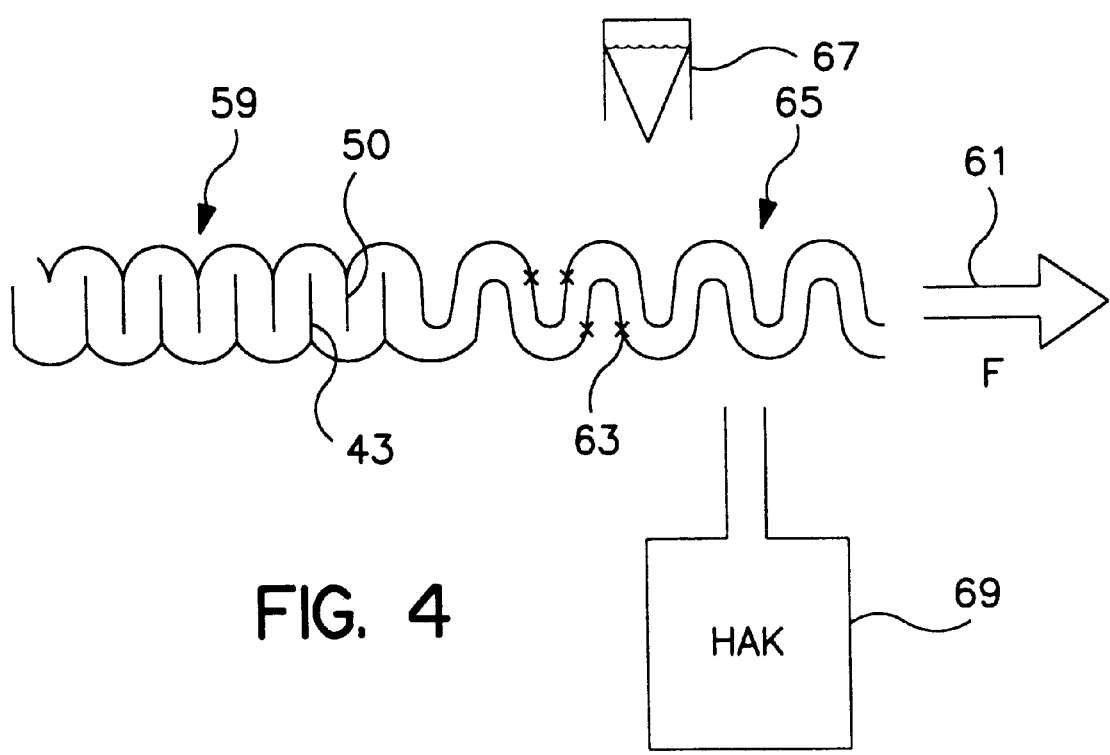
FIG. 4 is a schematic diagram of the method of this invention for producing materials having z-direction components for the second, or final, lofty web configuration.

FIG. 4 illustrates the method of the present invention in process, whereby a nonwoven web made according to the present invention in a first configuration, illustrated on the left hand side of the figure at reference number 59, is subjected to a controlled force F in the direction of the arrow 61 thereby breaking any inter-ridge 50 or intra-ridge 43 bonding of the first configuration as indicated by the "x" marks, e.g. 63 on the right hand side of the figure. During or after the time the web is placed in the second configuration, i.e., wherein the ridges are non-adhered to either themselves or one another, as illustrated on the right hand side of the figure at reference number 65, an adhesive may be applied by an adhesive system 67 to set the web in the second configuration. The adhesive may be in the form of liquid or additional fibers or the like and may be supplemented with the application of heat, for example by a hot air knife 69. Alternatively, the web may be set in its second configuration through the use of heat alone by a hot air knife 69, through-air bonding, or the like.

As prviously mentioned, the characteristics of the material produced in accordance with the method of this invention may be varied by varying such method elements as nip geometry, including the vertical distance between first moving surface 11 and second moving surface 12 as well as the extent of overlap between first moving surface 11 and second moving surface 12, vacuum strength and location, bonding mechanism, and speeds of the material entering and leaving nip 13. The type of fiber will also have an affect on the morphology of the web made. In addition, although the present invention generally produces a self-supporting lofty web, the end product may include a support structure or a second material 23, as shown being introduced into nip 13 from the unwind designated by reference numeral 17.

Figure 5:
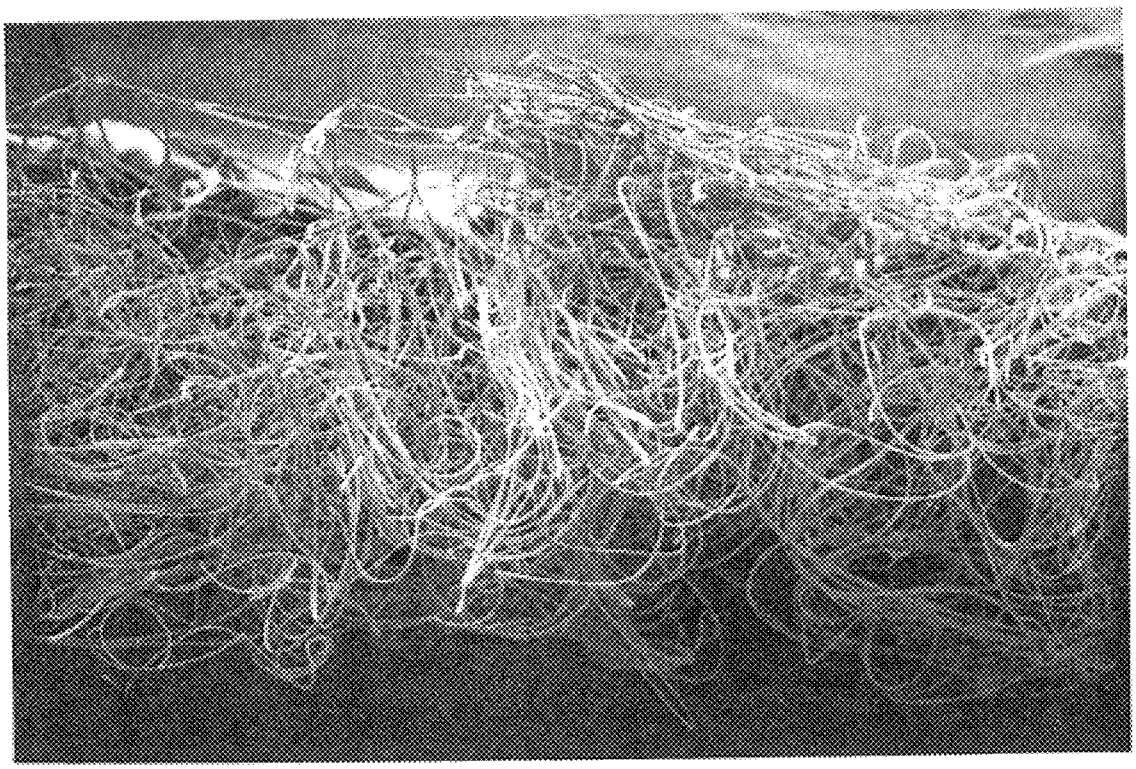
FIG. 5 is a photograph of a side view of a second nonwoven web according to the present invention having z-direction components without regular or discernable ridges as formed from side by side polymer, crimped fiber, base material.

FIG. 5 is a photograph of a side view of a nonwoven web produced in accordance with the method of the present invention, starting with a base material of substantially continuous individual fibers of the bicomponent side-by-side crimped type showing random intermingling of the fibers to the point of losing any regular shape and periodicity to the ridge structure of the web. No channels are evident within the web structure which would allow the easy passage of fluids in any direction through the web. A bonded carded web precursor material has also be found to work well for this embodiment of the invention.

Figure 6:
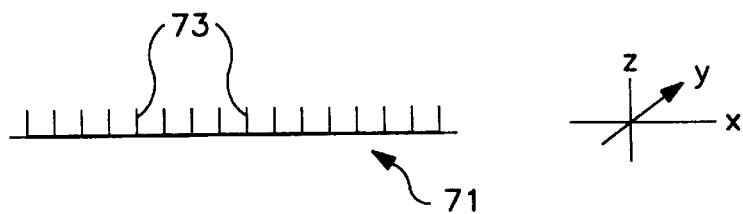
FIGS. 6 and 7 are schematic diagrams of a three dimensional forming surface for producing precursor materials having differential basis weight distributed in bands in the cross direction.
Figure 7:
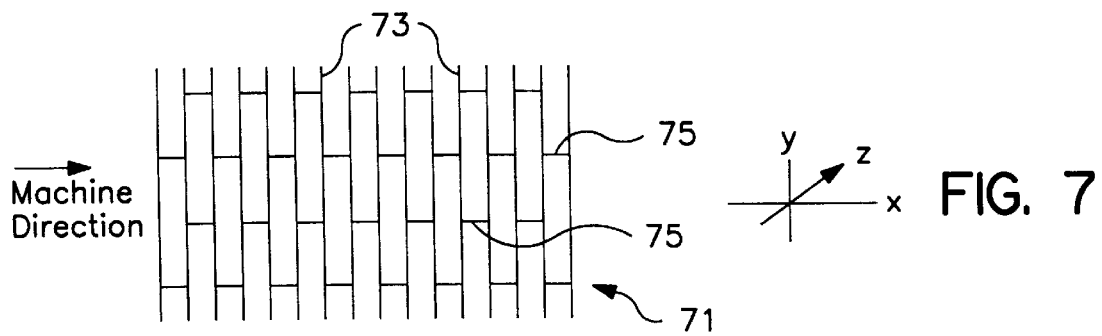

FIGS. 6 and 7 are schematic diagrams showing the method of this invention for producing precursor materials having differential basis weight and differential surface topography. A three dimensional forming surface 71 has thin raised lines 73 in the cross machine direction (y axis). The surface 71 may be a foraminous wire with raised wires in the cross direction interconnected with as few linking points 75 in the machine direction (x axis) as possible for stability of the forming surface. Alternatively, the surface 71 may be a formed membrane without cross links between the cross direction lines. The membrane is laminated or sewed to the circulating belts of forming machines in place of the more typical wire. The desired fiber type, whether substantially continuous or staple, is then deposited on the forming surface and fixed as by heat or adhesive, or both, to lock in the formed structure into the precursor material. The precursor material produced is in essence a negative of the forming surface 12 and exhibits areas of higher basis weight and bulk and areas of lower basis weight and bulk. Thus the precursor material is denominated as differential basis weight material. While differential basis weight material has been made in the past it is not believed that the small scale of basis weight differential and surface topography of the present teaching have been utilized.

Figure 8:
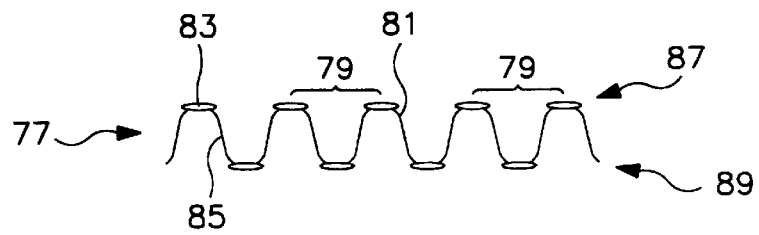
FIG. 8 is a diagram of a side view of one embodiment of the resultant lofty nonwoven web having z-direction components.

Referencing FIG. 8, after being processed according to the present invention the resultant lofty nonwoven web 77 shows the differential basis weight precursor material changing directions within a fold 79 at the junction 81 of the higher basis weight 83 and lower basis weight 85 material to impart the z-direction orientation to the resultant web 77. In this instance, both first and second major surfaces 87 and 89, respectively, of the x-y plane are composed of the higher basis weight material 83 with an interstitial material of lower basis weight material 85 lying in the z-direction.

Figure 9:
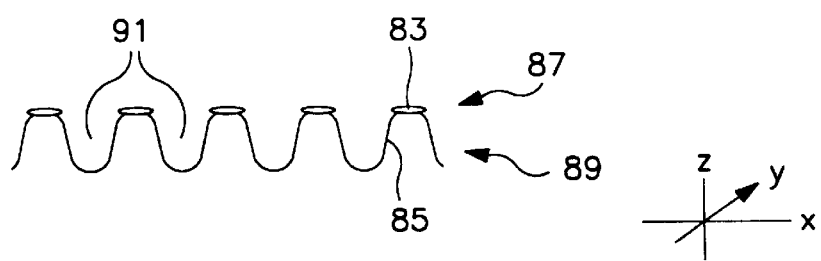
FIG. 9 is a diagram of a side view of a second embodiment of the resultant lofty nonwoven web having z-direction components.

FIG. 9 is a diagram of a side view of an alternative embodiment of the resultant lofty nonwoven web wherein the precursor and processing variables as discussed above have been adjusted to provide that only the first major surface 87 is composed of the higher basis weight material 83, with the interstitial material and second major surface 89 being composed of lower basis weight material 85. The resultant web has definite channels, collectively 91, extending in the cross machine direction.

Figure 10:
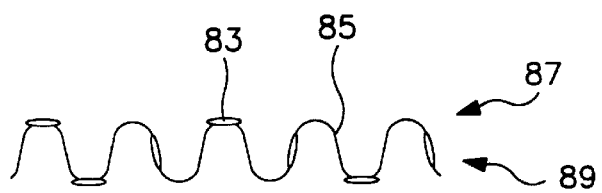
FIG. 10 is a diagram of a side view of a third embodiment of the resultant lofty nonwoven web having z-direction components composed of intermixed higher and lower basis weight materials.

FIG. 10 is a diagram of a side view of an alternative embodiment of the resultant lofty nonwoven web wherein the precursor and processing variables have been adjusted to provide that the z-direction components are composed of both higher basis weight 83 and lower basis weight 85 material.

Figure 11:
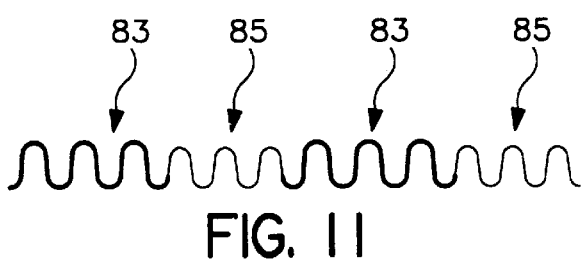
FIG. 11 is a diagram of a side view of a third embodiment of the resultant lofty nonwoven web having z-direction components composed of alternating areas of higher and lower basis weight materials.

FIG. 11 is a diagram of a side view of an alternative embodiment of the resultant lofty nonwoven web wherein the precursor and processing variables have been adjusted to provide that the z-direction components are composed of alternating folds of higher basis weight 83 and lower basis weight 85 material.

Potential applications for the nonwoven web of this embodiment include personal care absorbent articles such as diapers, training pants, incontinence garments, feminine care products including sanitary pads and napkins, all surge materials, loop for hook and loop, air filtration, liquid filtration, body scrub pads, oil sorb, industrial and baby wipes, insulation material, packaging material, and translucent or shading material for lamp shades or the like. In the case of filtration materials, the method of this invention greatly increases the surface area available for filtration.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for producing a material having z-direction folds comprising:

conveying continuous fibers on a first moving surface from the first moving surface to a second moving surface, the second moving surface traveling at a slower speed than the first moving surface, resulting in formation of a material having a plurality of z-direction folds on both surfaces of the material;

wherein the first moving surface and the second moving surface are perforate; and wherein the material is transferred from the first moving surface to the second moving surface using a controlled vacuum whereby the material is pulled in a direction of the second moving surface.

2. The method for producing a material having z-direction folds according to claim 1 further comprising:

positioning the first moving surface and the second moving surface to form a nip therebetween.

3. A method in accordance with claim 1 wherein the continuous fibers are selected from the group consisting of spunbond, meltblown, spunbond-meltblown-spunbond laminates, coform, spunbond-film-spunbond laminates, bicomponent spunbond, bicomponent meltblown, biconstituent spunbond, biconstituent meltblown, and combinations thereof.

4. A method in accordance with claim 1, wherein the first moving surface is traveling in a range of about 1.1 to about 7 times faster than the second moving surface.

5. A method in accordance with claim 1, wherein the first moving surface is a forming surface on which the fibers are formed.

6. A method in accordance with claim 1 wherein the fibers are lightly bonded.

7. A method in accordance with claim 1, wherein the material is bonded by at least one of an adhesive bonding process and a thermal bonding process.

8. A method in accordance with claim 1, wherein the material is transferred from the first moving surface to the second moving surface using a positive air pressure whereby the material is pushed in a direction of the second moving surface.

9. A method in accordance with claim 1, wherein at least one additional material is applied to a face of the material, forming a composite or laminate.

10. A method in accordance with claim 1, wherein the continuous fibers comprise a plurality of thermoplastic fibers.

11. A method in accordance with claim 1 wherein the first moving surface and second moving surface face opposing directions.

12. A method in accordance with claim 11 wherein the first moving surface and second moving surface have no directly opposing faces to form a channel.

13. The method of producing a material having z-direction folds according to claim 1 further comprising:
forming a resultant base material having a plurality of z-direction fiber loops therein and with no discernable ridges or channelization therein.

14. The method for producing a material having z-direction folds according to claim 13 wherein: the base material is a flat layer of nonfunctionally bonded substantially continuous fibers.

15. The method for producing a material having z-direction folds according to claim 13 wherein: the base material is a bonded carded web.

16. The method for producing a material having z-direction folds according to claim 13 wherein: the base material is a layer of crimped substantially continuous fibers.

17. The method for producing a material having z-direction folds according to claim 13 wherein:
the first moving surface has a vacuum associated therewith for holding the base material thereto.

18. The method for producing a material having z direction folds according to claim 13 wherein:
the second moving surface has a vacuum associated therewith for holding the resultant material thereto.

19. The method for producing a material having z-direction folds according to claim 13 wherein:
the second moving surface has a high vacuum associated therewith for transferring the base material from the first moving surface to the second moving surface.

20. A method for producing a material having z-direction folds comprising:
conveying continuous fibers on a first moving surface from the first moving surface to a second moving surface, the second moving surface traveling at a slower speed than the first moving surface, resulting in formation of a material having a plurality of z-direction folds on both surfaces of the material;
forming a bas material of a layer of substantially continuous fibers into a nonwoven web in a first configuration with the z-direction folds forming regularly shaped ridges occurring with regular periodicity in one of a machine or cross machine direction;
lightly fixing the ridges in the first configuration;
breaking the fixing of the ridges and resetting the ridges to a second predetermined configuration; and
fixing the ridge in the second configuration.

21. The method of claim 20 wherein the step of lightly fixing the ridges in the first configuration further includes applying an adhesive to the base material after forming the first configuration.

22. The method of claim 20 wherein the step of lightly fixing the ridges in the first configuration further includes applying an adhesive to the base material before forming the first configuration.

23. The method of claim 20 wherein the step of lightly fixing the ridges in the first configuration further includes applying heat to the web while in the first configuration.

24. The method of claim 20 wherein the step of resetting the ridges to a second further includes a controlled stretching of the web to the second configuration.

25. The method of claim 20 wherein the step of fixing the ridges in a second configuration further includes bonding the web to a lamina while in the second configuration to thereby set the ridges in the second configuration.

26. The method of claim 20 wherein the step of fixing the ridges in a second configuration further includes applying heat to the web while in the second configuration.

27. The method of claim 20 wherein the ridges occur with regular periodicity in the machine direction.

28. The method of claim 27 wherein the ridges extend across the web in the cross machine direction.

29. The method of claim 20 wherein the step of fixing the ridges in a second configuration further includes applying an adhesive to the web while in the second configuration.

30. The method of claim 29 wherein the step of fixing the ridges in a second configuration further includes applying heat to the web while in the second configuration.

31. The method of claim 20 wherein the step of fixing the ridges in a second configuration further includes applying additional fibers to the web while in the second configuration.

32. The method of claim 31 wherein the additional fibers are thermosetting fibers.

33. The method of claim 32 including the further step of applying heat to the additional fibers.

* * * * *